US008443826B2

(12) United States Patent
Tatarek

(10) Patent No.: US 8,443,826 B2
(45) Date of Patent: May 21, 2013

(54) DEMAND VALVE FOR GAS MIXING

(75) Inventor: Andrew Tatarek, Hampshire (GB)

(73) Assignee: Concept 2 Manufacture Design OCD Ltd., Hampshire (GB)

( * ) Notice: Subject to any disclaimer, the term of this patent is extended or adjusted under 35 U.S.C. 154(b) by 594 days.

(21) Appl. No.: 12/601,421

(22) PCT Filed: May 23, 2008

(86) PCT No.: PCT/GB2008/050375
§ 371 (c)(1),
(2), (4) Date: May 21, 2010

(87) PCT Pub. No.: WO2008/146038
PCT Pub. Date: Dec. 4, 2008

(65) Prior Publication Data
US 2010/0236635 A1 Sep. 23, 2010

(30) Foreign Application Priority Data

May 25, 2007 (GB) .................................. 0710048.0

(51) Int. Cl.
*G05D 11/02* (2006.01)

(52) U.S. Cl.
USPC ............. 137/98; 137/506; 137/510; 137/607; 137/908; 137/114; 128/203.12; 128/205.24

(58) Field of Classification Search
USPC ................. 137/114, 494, 506, 510, 607, 907, 137/908, 599.03, 456, 98, 100, 111; 128/203.12, 128/204.26, 205.11, 205.24; 251/40, 58, 251/61, 231, 232, 239, 244
See application file for complete search history.

(56) References Cited

U.S. PATENT DOCUMENTS

| | | | |
|---|---|---|---|
| 2,534,959 A | | 12/1950 | Brown et al. |
| 3,348,538 A | * | 10/1967 | Benzel ...................... 128/204.26 |
| 3,357,447 A | * | 12/1967 | Zarichansky ................. 137/494 |
| 4,072,148 A | * | 2/1978 | Munson et al. .......... 128/205.11 |
| 4,306,584 A | * | 12/1981 | Schlobohm .................... 137/494 |
| 4,714,090 A | * | 12/1987 | Sampson ....................... 137/636 |
| 4,827,965 A | * | 5/1989 | Wates ............................. 137/88 |
| 5,544,674 A | * | 8/1996 | Kelly ............................... 137/98 |

FOREIGN PATENT DOCUMENTS

| | | |
|---|---|---|
| GB | 949 221 | 2/1964 |
| GB | 949222 | 2/1964 |
| GB | 2 178 964 | 2/1987 |

* cited by examiner

*Primary Examiner* — Stephen M Hepperle
*Assistant Examiner* — Ian Paquette
(74) *Attorney, Agent, or Firm* — Drinker Biddle & Reath LLP

(57) ABSTRACT

A demand valve for gas mixing comprises two or more flow control valves that are connected to separate gas supplies. The demand valve includes a common actuation mechanism, such as a diaphragm arranged to displace levers, each of which, in turn, opens and closes proportionally in a substantially constant ratio a respective flow control valve. Inhalation flow drawn through an outlet causes displacement of the diaphragm and hence opening of the flow control valves. Gas from the separate supplies is therefore mixed in a main chamber to a substantially constant composition, regardless of the flow rate demanded, before being dispensed via the outlet.

22 Claims, 11 Drawing Sheets

DEMAND VALVE FOR GAS MIXING

The present invention relates to a valve for allowing gas mixing on demand and to a method of mixing gases for inhalation by a user.

Demand valves are used in a variety of fields in order to supply gas to a user in response to the user's inhalation. Medical applications include the supply of 100% oxygen gas for resuscitation or for treatment for smoke inhalation. Breathing apparatus regulated by a demand valve is also commonly used in diving or escape equipment. In the diving field a demand valve is more commonly referred to as a gas regulator, but it performs the same function as for the medical field. That is, it supplies gas at a flow rate that essentially matches that demanded by a user.

Typically a demand valve is connected to a gas supply regulated to a medium pressure, for example 2-10 bar, such as from a regulator on a cylinder or gas pipeline. The outlet of the valve is connected to a mask, mouthpiece or other interface, which is placed over a user or patient's mouth or nose. As the user inhales, the valve supplies gas flow matching the demand, maintaining a roughly constant pressure at the outlet that is in keeping with what can readily be drawn by a patient (in the region of 0-1000 Pa below atmospheric pressure).

Numerous types of demand valve are known that can be used to deliver pure or pre-mixed gases such as oxygen, air, helium-oxygen mixture (for diving) or oxygen-nitrous oxide mixture (for pain relief). Such gases are generally available either from a cylinder with a suitable regulator or from a pipeline supply in which compressed gas is piped to a wall socket. Examples of demand valves are described in, for example, GB2432123, GB2195900 and GB2274595.

A disadvantage of such prior art demand valves is that they are suitable only for use with a single gas supply. That is, they must be connected to a single pressure source. Individual gases are of course readily available in a cylinder or via a pipeline supply, however only a limited number of pre-mixed gas combinations are currently available. Indeed, for example, US regulatory requirements forbid the pre-mixing of oxygen and nitrous oxide, which is a common gas mixture used for pain relief. The gas mixture must therefore be prepared just prior to use, using the individual gases from two sources.

Prior art attempts to mix gases on demand from different pressure sources have largely been unsuccessful due to the strict tolerances required. It is critical that a device that is designed to mix gas on demand will mix the gas in the same proportions across the range of inhalation flows experienced during a respiratory cycle and for different users.

It has proved very difficult to manufacture two demand valves that will respond in the same way to the same inhalation flow. Inevitably, one valve will open sooner than the other resulting in the supply of one gas in advance of the second. Even after both valves have opened, it is difficult to control sufficiently the degree to which both are held open. This affects critically the composition of the gas mixture, to the extent that the mixture dispensed may not have its desired therapeutic effect. Without consistency of behaviour, it is not possible to construct a device that draws gases proportionally from two pressure sources via respective demand valves. A single demand valve requires a single source and therefore pre-mixing of the gases if it is to deliver a gas mixture.

A second approach taken in the prior art is to provide the separate gas supplies with respective regulators. The regulators are set to dispense their respective gases at the same pressure and to the same demand valve. Sometimes an orifice is included between the regulators and the demand valve in an attempt to balance the flow further. This approach has also proved unsatisfactory due to the strict tolerances required and to the sensitivity of the device to friction variations between the regulators. At the critical opening phase in particular, i.e. when the gas is first dispensed, simultaneous opening of the regulators is very difficult to achieve with any degree of consistency. Moreover, the flow rate supplied by regulators from a single source varies somewhat as the supply empties. In trying to match the flow rate from two sources, this variation is sufficient to affect over time the composition of the gas mixture dispensed. Finally, the orifice approach to balancing flow does not work across the entire flow range. An orifice that is capable of passing the maximum flow will have insignificant resistance at and close to the opening point.

In summary therefore, prior art demand valves work well when dispensing gas from a single source in response to inhalation by a user. There is however an identified need for dispensing a mixture of gases to a user on inhalation. There are problems inherent in adapting two demand valves or regulators to be responsive to a single user demand. In order to ensure consistent dispensing of the desired gas composition, the valves or regulators must be arranged to open simultaneously and to ensure that they remain open to a similar extent over their operating range. The strict tolerances placed on valve design and manufacture by these requirements have meant that all prior art attempts to implement a demand valve for gas mixing have proved unsatisfactory.

The present invention provides a demand valve for gas mixing, the valve comprising at least two gas connection channels, each containing a respective flow control valve for supplying gas to a main chamber wherein the valve includes an actuation means that is responsive to a pressure change in the main chamber. The valve is characterised in that the actuation means is a common actuation means in that by a single movement it is operable to displace sealing means from a seat of each flow control valve so as to open and close proportionally in a substantially constant ratio the at least two flow control valves.

Use of a common actuation means to open and to control the degree of opening of separate flow control valves, which respectively control flow from separate gas sources, represents a significant improvement over the consistency of performance that has previously been achievable with multiple valves. This represents a significant improvement over the prior art in that a major source of uncertainty is eliminated: non-alignment of valve opening and closing. If the actuation means is displaced a small amount, the two or more valves will open to a predetermined extent. Further displacement results in the valves opening further, but to a degree that is in substantially constant ratio. Similarly, subsequent movement of the actuation means in a reverse direction results in the valves being closed to some extent, but again in substantially constant ratio. The common actuation means also represents a significant improvement over the prior art in the pursuit of simultaneous opening.

By ensuring that the separate valves are open in a substantially constant ratio, the composition of gas mixture can be maintained. For example, if the design of two flow control valves is such that, when fully open, a first valve dispenses three times as much gas as a second, the gas mixture with both valves from fully off to fully on will be in the ratio 3:1.

The actuation means can also be set however to open the first control valve to, say, half the extent of the second. That is, the gas mixture, assuming identical valves, will be in the ratio 1:2. Regardless of whether the second valve is fully open, half open or 10% open, the first valve will be half open, 25% open or 5% open respectively, thereby maintaining the gas ratio at the required level of 1:2.

Of course, it is possible to combine the two scenarios above to provide further flexibility. If the valve design is such that the fully on ratio of gases is 3:1 and the actuation means is set to provide opening in the ratio 1:2, then overall gas composition will be in the ratio 3:2.

As indicated above, gas flow rate into the main chamber, and hence composition of the mixture, can be adjusted by varying any of a number of design parameters. For example, the seat of one control valve may have a different diameter compared with the other valve(s). The pressure at which gas is supplied and the physical properties of the gases used will also affect flow of the gas, and hence overall composition, through the control valves for a given fractional opening.

In applications such as this in which it is important to have consistent and fine control of the opening and closing of a seat, direct actuation valves are very much preferred. A direct actuation valve is one in which movement of the diaphragm, or other actuation means, is communicated directly to a movement of the valve seal towards or away from its seat. The alternative servo-controlled valves have no direct link between actuation means and seal movement. Inevitably there will be a time lag and a reduced correlation between actuation movement and flow rate. Accordingly the characteristics of different valves are far more difficult to match over their full range of operating flow rates, or the full range of flow rates required for their intended application, which makes them inherently far less suitable for use with this invention.

Each flow control valve is ideally a lever valve operated by a respective lever extending from a central region of the common actuation means.

There are many types of known lever valve that may be used with this invention. In such valves, one end of a lever is moved by the actuation means, such as a diaphragm, about a pivot point. The other end of the lever has a shorter range of movement as it opens and closes a seat of a valve. The lever valve is one example of a direct actuation valve in that control of the lever is directly linked to the opening and closing of an orifice through which gas flow is delivered.

The mechanical benefit of the lever is that it requires a relatively large movement at the actuation end that results in direct, fine control of the opening and closing of the seat. Thus, any errors of misalignment or differences in manufacturing of multiple valves, will be proportionally of less consequence to the flow control behaviour of each. Fine control of the opening and closing of the seat may alternatively be achieved by use of a larger diaphragm to move a seal directly towards and away from the seat, but this is a far less practical implementation without the benefit of error reduction.

In a lever valve, adjustment of flow parameters may also be achieved by adapting the length of lever. In the example referred to above, the first control valve may be set to open to half the extent of the second if it is operated by a lever that is twice as long.

In a preferred embodiment, each control valve is a tilt valve. As used herein, a tilt valve is a specific example of a lever valve in which lateral movement of the actuation end of the lever directly affects the degree of tilt between a sealing cap and the valve seat. That is, effectively a hinged opening is provided between seat and sealing cap. The benefit of such valve is that, when used in control valves, gas flow is approximately proportional to the movement of the lever.

The lever of each tilt valve may extend from a central region of the actuation means to a respective cap. The cap may comprise a sealing face for sealing against the seat and locating means for holding the cap centrally in a bore of the gas connection channel wherein lateral movement of one end of the lever by the actuation means effects a pivotal tilt of the cap within the bore such that the sealing face lifts partly off the seat.

The lever may extend through the seat of the respective flow control valve, which arrangement suits a valve arranged to seal with supply pressure. Alternatively, if the seal is required to close the seat against supply pressure, the lever will not pass through the seat and, a spring or other biasing means is used to bias the seal to overcome, just, the pressure of the supply.

In embodiments in which the tilt valve seals with the supply pressure, the tilt valve may still include biasing means, such as a spring, set to bias the cap against the seat, which assists in forming a more effective seal when the valve is closed. This is essential for instances in which the gas pressure alone is not sufficient to close the tilt valve, for example if a very low gas pressure is used to deliver a low proportion of a particular gas through the tilt valve in question. It is also desirable to prevent the seal rattling against the seat in case of rough handling and to prevent the seal being pushed rapidly against the seat in the event that the gas pressure is switched on rapidly.

The tilt valve is ideally made with components whose movement is as free from friction as possible. This minimises the inhalation pressure required to move the diaphragm or other actuation means, reduces wearing and also reduces the possibility of the valve from sticking open. All of these are important to uniformity. If one tilt valve in a gas mixing assembly sticks open, then clearly the required gas composition will no longer be delivered. If one valve wears to a different extent than another over time its behaviour will start to differ. This can affect demand valve performance to the extent that the required composition of gas mixture may no longer be delivered.

While the tilting of the cap of the tilt valve is necessary and desirable, a rotation about the axis of the lever is not. Although the cap/lever assembly is nominally symmetrical, in reality manufacturing and assembly differences will inevitably occur: the lever will not necessarily be exactly central to the cap nor exactly perpendicular to its sealing face. Adjustment means may be included in the demand valve to enable adjustment of lever/cap positions for each valve in order to ensure that flow rates passed through the various flow control valves are matched to within tolerance. Once set however, a rotation of the cap/lever may cause alignment to fall out of tolerance and valve function to be compromised. In order to inhibit rotation therefore, a protrusion such as a pin or pins is located in the bore of the gas connection channel for interengagement with the locating means of the cap. The locating means of the cap is preferably in the form of a series of slots or protrusions.

The sealing face of the cap may include an insert made of a harder material than that of the remainder of the cap. Such hardened material may be hardened, ground and polished steel or, preferably, an industrial jewel, such as ruby or sapphire, or ceramic. This insert provides a two fold advantage. First, it can be made extremely flat, which permits a good seal to be formed on contact. This is to be contrasted with a more resilient material such as rubber, which must be compressed in order to effect a good seal, requiring an additional closing force to be applied. This gives a nonlinear component to the behaviour of the seal (at its closure point) in relation to movement of the actuation means, which, in turn, reduces the likelihood of uniformity being achieved for multiple valves. Secondly, the seal will inevitably show some degree of wear over time, generally at the position it presses against the seat. As mentioned previously, wearing will not occur consistently across a set of matched valve assemblies and it will therefore contribute to a loss of uniformity over time. Use of a hard material on the contacting surface of the seal reduces the likelihood of wearing and its undesirable consequences. Alternatively, the whole cap may be made of the harder material, but as this material is generally more expensive than that of the cap (typically a plastic material), this is not the preferred economic option. The composite construction, with insert, provides a readily-manufactured component that balances performance with cost.

In embodiments in which the common actuation means is a diaphragm, a contact pad may be attached to the diaphragm and positioned so as to contact the levers that control operation of the flow control valves. The contact pad may include one or more apertures through which the levers extend. If the levers extend through respective apertures then this permits longer lengths of levers to be held. This is advantageous as it reduces the likelihood of the levers being removed accidentally from the aperture if they are pushed back for any reason.

The demand valve may further include guidance means connected to the diaphragm whereby tilting of the diaphragm is hindered. If the diaphragm tilts during flexing it is likely to move one lever further than another. The flow control valve operated by that lever would accordingly open further and deliver an increased proportion of gas to the mix.

In another embodiment, the gas mixing demand valve includes a pressure detector located in one of the gas connection channels and acting on the diaphragm or common actuation means and arranged such that if the pressure in the gas connection channel drops below a predetermined level, the actuation means is moved to close the at least two flow control valves. This provides a fail safe mechanism by which flow is completely cut if one gas supply runs out, and an operator can be alerted. Generally, the pressure detector would be connected to the supply of a critical gas, most likely oxygen. Then, if the oxygen flow ceases, the fail safe prevents 100% of another gas being delivered to the user; the valve would simply be shut.

Alternatively, the demand valve may include first and second regulators located in respective gas connection channels, the first regulator being piloted by the second such that the output of the first regulator is substantially matched or proportional to that of the second. The regulators are further arranged such that if the output of the second reducer falls below a predetermined level, the output of the first reducer falls to zero.

Various geometrical arrangements of gas connection channels around the main chamber are envisaged. For example, the valve may contain two gas connection channels located at opposite sides of the main chamber. Alternatively, the pair of channels may be on the same side or even adjacent each other. Or three, four or more channels may be distributed around the chamber. Of course, even if, for example, a four-channel valve is used, it need not be attached to four gas supplies. Some channels may remain unused, making this a more versatile embodiment of this invention.

In a second aspect, the present invention provides a method of mixing gases on demand, the method comprising the steps of:
(a) changing pressure in a main chamber of a demand valve in response to a user's respiration; and
(b) moving a common actuation means in response to the pressure variation at step (a), the common actuation means being operable to open and close proportionally in a substantially constant ratio at least two flow control valves, the at least two flow control valves being pre-positioned in respective gas connection channels taking gas from respective independent sources.

In a third aspect, the present invention provides a sealing means for use in a tilt valve comprising a lever extending from a cap, the cap comprising a sealing face for sealing against a seat of the tilt valve and locating means for holding the cap centrally in a bore of a gas connection channel wherein lateral movement of one end of the lever effects a pivotal tilt of the cap within the bore such that the sealing face lifts partly off the seat characterised in that the sealing face includes an insert of a harder material than the remainder of the cap. The insert may be annular and, preferably, is of a material that gives a flat and smooth surface such as an industrial jewel, tungsten carbide or a ceramic. A flat, smooth surface may be obtained by grinding and polishing or other appropriate means.

Embodiments of the invention will now be described by way of example only and with reference to the accompanying drawings.

Figure 1:
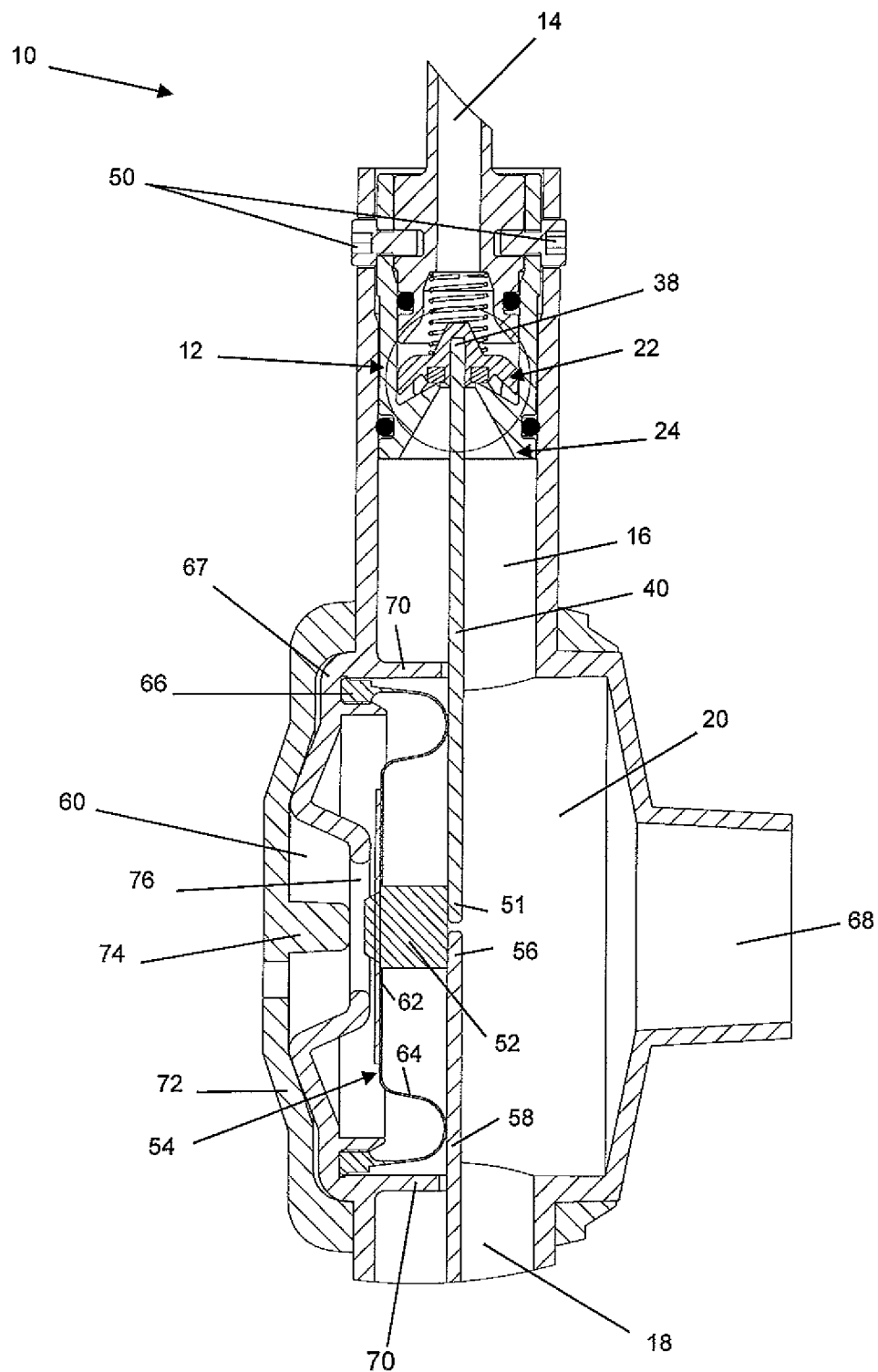
FIG. 1 is a schematic illustration, viewed in cross section, of part of a first embodiment of a demand valve in accordance with this invention when in a closed configuration.

With reference to FIG. 1, there is shown a demand valve 10 for gas mixing. The demand valve comprises first 12 and second (not shown) tilt valves located between gas connection channels 14 and input channels 16, 18 that are in fluid communication with a main chamber 20. For clarity, only one tilt valve 12 and gas connection channel 14 is illustrated in this Figure but it is to be understood that a second valve (which may be the same or of a different design to the first) is located between a second gas channel and the input channel 18 to the other side of the main chamber 20 (see FIG. 3 in which two valves are shown).

The gas connection channels 14 are connected to the pressure side of the tilt valve 12 and are fed by any suitable source of pressurised gas. Suitable sources may be, for example, a cylinder via a reducer, a direct link to a piped supply or a piped supply via a hose. Alternatively, the channels 14 may be integrated into a reducer on a cylinder or any other suitable supply of gas.

Figure 2:
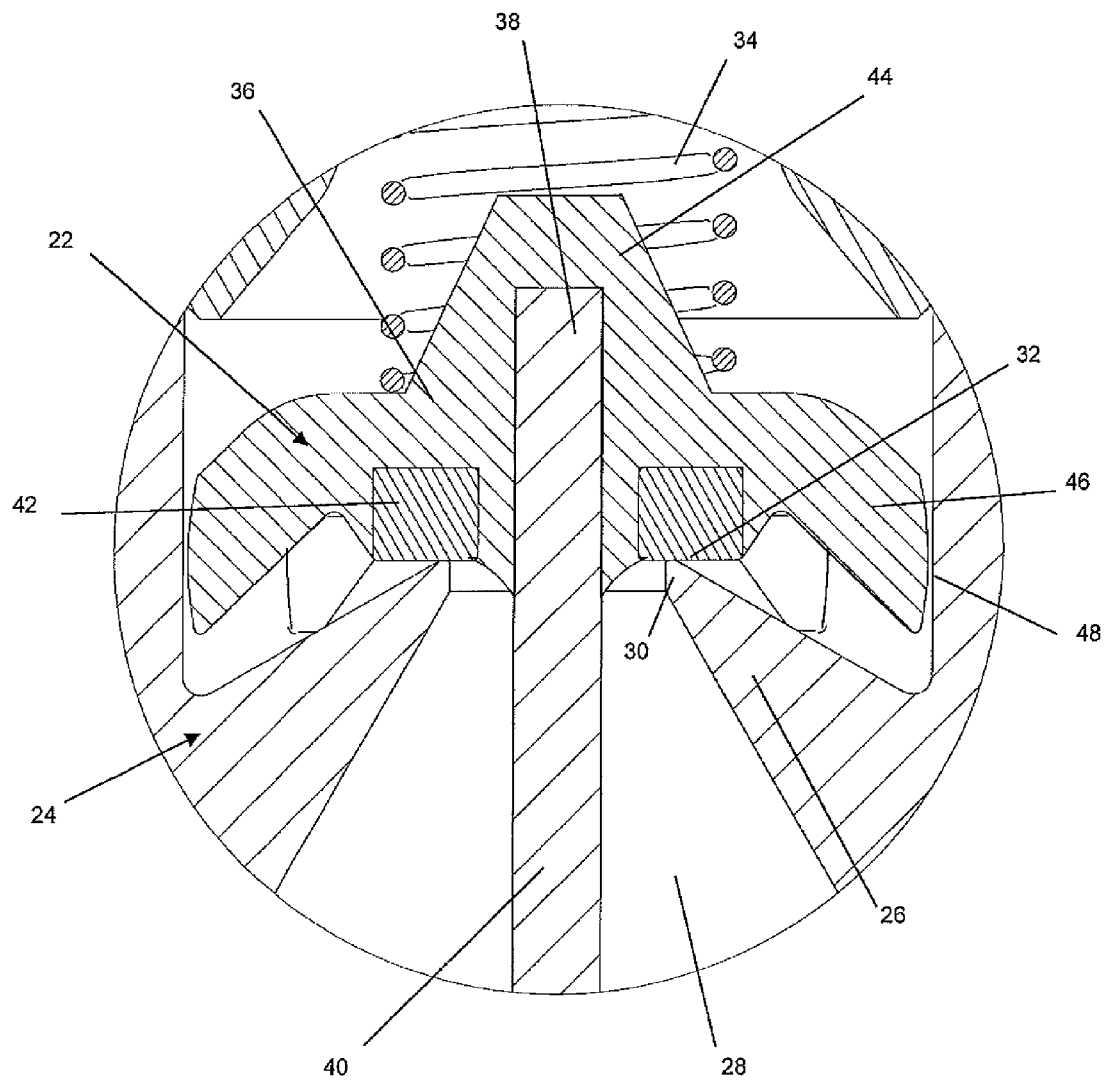
FIG. 2 is an enlarged portion of a sealing region of the tilt valve component of the demand valve shown in FIG. 1.

With reference to both FIGS. 1 and 2, the tilt valve 12 comprises a sealing member 22 for sealing against a seat 24. The seat 24 includes a truncated cone 26, protruding towards the gas connection 14, with a passage 28 through its centre. At its tip, the truncated cone 26 surrounding the passage 28 forms a narrow flat annular sealing face 30, on the gas supply side. The sealing member 22 has a flat sealing face 32, which, when the valve is closed, is biased against the annular sealing face 30 of the seat by a spring 34 so as to prevent gas flow through the passage 28. The valve 12 is opened and closed by tilting the sealing member 22 about a pivot point on the annular sealing face 30 of the seat, so as to create a variable-sized aperture. The shape of the aperture will be approximately that of a cylindrical tube, cut at an angle. Accordingly, it will be a wedge or taper shape: zero at the pivot and a maximum diametrically opposite the pivot.

The sealing member 22 comprises a cap 36 formed about one end 38 (the sealing end) of a stiff lever 40. The cap 36 is formed of injected plastic (for example ABS or Acetal) or of metal surrounding an annular insert 42 of hardened material such as an industrial jewel (for example, sapphire or ruby) or hardened and ground steel. The cap 36 is shaped to have, in addition to the flat sealing face 32, a roughly conical head 44 and locating features 46. A lower surface on the insert 42 is in line with the sealing face 32. When the valve 12 is closed, it is the insert 42 surface that seals against the annular sealing face 30 of the seat. The cap 36 is of a diameter that gives it a clearance fit against an inside diameter (bore) 48 of the seat 24. By the term "clearance fit" it is to be understood that the cap fits snugly inside the bore 48 of the seat, without or barely touching its sides. This serves to locate the sealing member 22 substantially centrally in the bore.

The locating features 46 (see FIG. 5) are approximately spherical in external profile, with the sphere centred on a point at the centre of the sealing face 32. In this way, the spherical profile of the cap presented to the walls of the bore 48 will remain approximately constant as it is pivoted about a point on the annular sealing face 30 of the seat. This will prevent the sealing member 22 sliding against the seat 24 as the valve 12 tilts and opens. The locating features 46 further include a series of holes or slots through their length to allow gas to pass freely from the gas connection channel 14 to the seat 24. In the embodiment shown, slots are illustrated, resulting in the formation of locating legs 49 (see FIG. 5).

When supply pressure is applied through the gas connection channel 14, the pressure over the sealing member 22 on the area 30 of the seat 24 is, aided by the bias of the spring 34, sufficient to push the sealing member 22 against the seat 24, closing the passage 28 and preventing gas flow between the seat 24 and the sealing member 22.

Outside the tilt valve 12 assembly, a pair of o rings, or similar, provide seals between the seat 24 and gas supply and between the seat 24 and main body of the demand valve 10. Screws 50 retain the external connection between the gas connection channel 14 and seat 24. The screw heads are a close fit in the body of the demand valve and so further hold the seat 24 to the body. The internal end of each screw fits into a circumferential groove in the gas connector and thus retains the connection in such a way that any gas supply hose or other piping can freely rotate.

The stiff lever 40 is typically made of metal such as stainless steel or aluminium with a round profile. Alternatively, it may take the form of a strip made from sheet metal, or other suitable construction. The lever 40 is rigidly retained within the cap 36 and is aligned as close to perpendicular to its sealing face 32 as is possible using available manufacturing capabilities. The lever 40 extends through the passage 28 in the seat and through the input channel 16 to a central region of the main chamber 20, where its actuation end 51 is aligned with a contact pad 52 of a diaphragm 54. An actuation end 56 of a second lever 58, which extends to the second tilt valve (not shown in the Figure), is also aligned with the contact pad 52 of the diaphragm 54.

The diaphragm 54 seals between the main chamber 20 and a secondary chamber 60, which is vented to atmosphere via any suitable arrangement of holes/passages, as is well known in the art. The diaphragm 54 comprises a stiff central portion 62 and a thin, flexible, resilient outer portion 64. Typically, the central portion 62 is made of an aluminium disc and the outer portion 64 of silicone rubber or thermoplastic elastomer, although other known materials that are suitable for the function can be used. An external rim 66 of the diaphragm is clamped between an outer wall of the valve and a retaining wall 67 in such a way that it forms a seal between the main chamber 20 and secondary chamber 60.

The contact pad 52 is typically a rubber pad that extends on the main chamber 70 side of the diaphragm 54. The pad 52 may be integral with the diaphragm or attached to it by any suitable means such as a screw. When the diaphragm 54 is in its relaxed state, the tilt valves are closed and the contact pad 52 rests at a point just short of contact with the actuation ends 51, 56 of the stiff levers 40, 58.

The basic principle of operation of the demand valve 10 will now be described with reference to FIGS. 1 to 4. When not in use (dispensing gas), the tilt valves 12 are closed and the pressure in the main chamber 20 is atmospheric. This is balanced by atmospheric pressure in the secondary chamber 60 and the diaphragm 54 is accordingly relaxed. This situation is shown in FIGS. 1 and 2.

Figure 3:
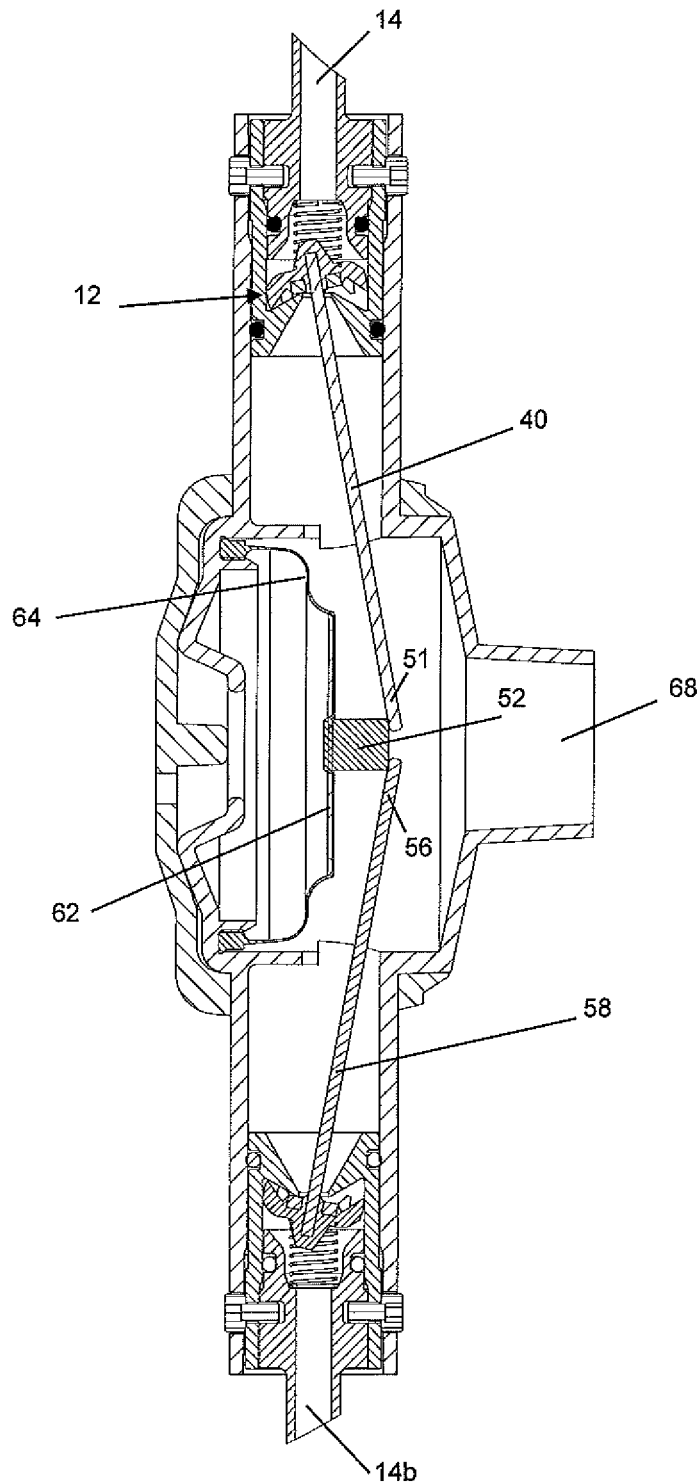
FIG. 3 is a schematic illustration, viewed in cross section, of the demand valve shown in FIG. 1, when it is in an open configuration, such as when supplying a gas mixture.
Figure 4:
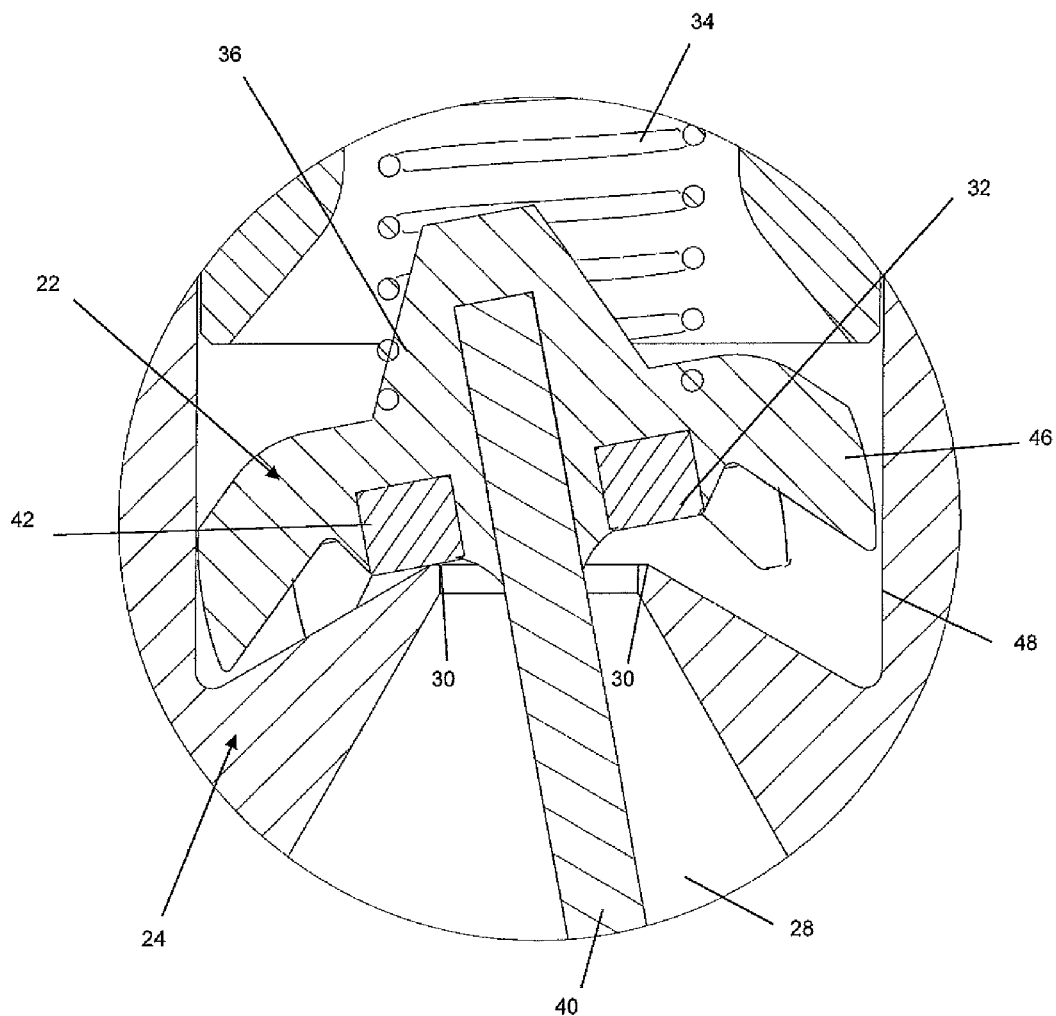
FIG. 4 is an enlarged cross-section portion of a sealing region of one of the tilt valve components of the demand valve configured as shown in FIG. 3.

FIGS. 3 and 4 illustrate the demand valve 10 in an open position. In these figures, components common to those of the closed configuration of FIGS. 1 and 2 are like referenced. It is noted that, for completeness, FIG. 3 illustrates two tilt valves 12 with their respective supply channels 14, 14b connected to the main chamber 20, the second valve being omitted from FIG. 1 in order to more clearly illustrate the internal structure of a single valve.

When a user inhales through a mask or other patient/user interface, air is drawn from the main chamber 20 via outlet 68 and the pressure drops. The diaphragm 54 is displaced into the main chamber and the contact pad 52 pushes against the actuation ends 51, 56 of the tilt valve levers 40, 58. Each lever 40, 58 is pivoted about a point on the annular sealing face 30 of its respective seat 24, and the cap 36 rotates in the bore 48 of the seat. This rotation lifts the sealing face 32 of the cap upwards away from the annular sealing face 30 of the seat at a side diametrically opposite the pivot point (see FIG. 4). The seal is opened and so the difference between supply pressure and atmospheric pressure will cause gas to flow through the open area between seat 24 and seal 22. From there, gas flows along the input channels 16, 18 and into the main chamber 20 for inhalation by a user through the outlet 68.

If the flow drawn through the outlet 68 increases (i.e. a greater inhalation-induced pressure drop), the diaphragm will flex further into the main chamber 20, causing the levers 40, 58 to tilt further and so open the valves 12 further. This permits increased flow from the gas supply, which therefore compensates for the increased flow drawn from the outlet and pressure in the main chamber 20 is maintained. In this way, a stronger inhalation flow results in an increased amount of gas being dispensed i.e. the valve operates according to demand. Ideally, higher flow would be delivered in direct proportion to the increase in demand. In reality however, the stiffness of the resilient portion 64 of the diaphragm, the resistance of the outlet 68 and other factors will mean that a greater negative pressure may be required to draw proportionally more flow.

If the flow drawn through the outlet 68 decreases, the pressure in chamber 20 will increase as supply gas flows through the open tilt valves 12. The stiff portion 62 of the diaphragm is drawn back towards the secondary chamber 60 with the result that the levers 40, 58 tilt less and the open area through the valves 12 is decreased. Flow of supply gas is reduced, again balancing the drop in demand. Finally, as the inhalation-induced pressure falls back to the point required to just open the valves (cracking pressure), the seats will close. The configuration of the valve 10 returns to that shown in FIGS. 1 and 2.

The diaphragm 54 must meet certain design criteria to enable it to exert sufficient force on the actuation ends 51, 56 of the levers in response to a minimum expected inhalation pressure drop to open the tilt valves 12.

The force $F_{dia}$ required to be exerted by the diaphragm 54 in order to begin the tilt required to open a single tilt valve 12 is calculated from:

$$F_{dia} = \frac{1}{L_{lever}}(F_{seal} \times L_{seat})$$

where $L_{lever}$ is the length of the lever 40 from its contact point with the diaphragm 54 to the pivot point on the seat 24; $F_{seal}$ is the force with which the sealing member 22 is pushed against the seat 24; and $L_{seat}$ is the distance from the pivot point of the sealing member 22 on the seat 24 to the centre of the seat i.e. the length of the lever over which this load $F_{seal}$ is acting. That is, the total torque that the lever 40 has to overcome to start to tilt the sealing member 22 is $F_{seal} \times L_{seat}$.

$F_{seal}$ can be calculated from:

$$F_{seal} = P_{sup} \times A_{seat} + F_{spring}$$

where, $P_{sup}$ is the gas supply pressure, $A_{seat}$ is the area of the annular sealing surface 30 of the seat and $F_{spring}$ is the biasing force of the spring 34.

The sum of the forces $F_{dia}$ for each tilt valve 12 produces a total force that has to be exerted by the diaphragm to begin to open all the tilt valves 12. This total force divided by the effective area of the diaphragm (typically taken as being the area of the average diameter of the resilient portion 64), gives the negative pressure in the main chamber 20 that has to be applied to the diaphragm 54 to start to tilt the lever 40 and thereby to start to deliver flow. This is termed the "cracking pressure" of the demand valve.

Note that if another type of lever valve was used with this invention, the detail of the geometry would of course be different, but the same type of analysis of moments would apply.

Figure 10:
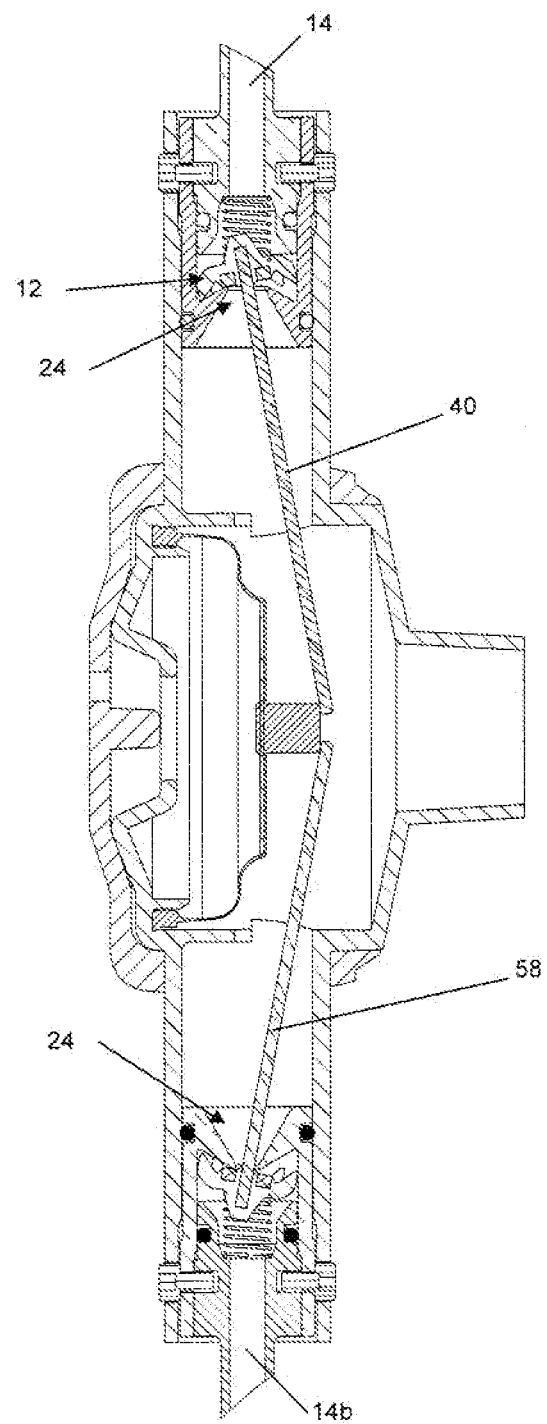
FIG. 10 is a schematic illustration, viewed in cross section, of an alternative embodiment of a demand valve of this invention, this embodiment having two valve seats of different sizes.

As indicated above, $P_{sup}$, $A_{seat}$, $L_{lever}$, and $L_{seat}$ all critically affect the amount of flow that is drawn through the demand valve. That is in constructing a demand valve with multiple inputs arranged to deliver different gases many possible design options are available to adjust the relative flow of each gas. The movement of the diaphragm 54 in response to gas flow through the outlet 68 will displace the actuation ends of the levers 40, 58 to the same extent, but thereafter the response of each valve can be varied. For example, the seat of one valve may be of a different area to another (see seats 24 shown in FIG. 10). One lever may be, say, half the length of another with the result that the valve operated by the shorter lever will open twice as much as the other. The valves may be connected to gas supplies at different pressures in order to permit further adjustment of relative flow. The result is a notable flexibility in arranging for the most effective gas mixture to be delivered to a user. This is particularly important for drug delivery in which different patient's body mass as well as their condition will determine the optimum drug combination for therapy.

In order to achieve accurate gas delivery ratios, regardless of the design parameters indicated above, two critical factors remain. It is important that first both (or all, if more than two) the tilt valves start to tilt simultaneously and that secondly, the degree of lever deflection at the contact point between lever 40, 58 and diaphragm 54 is largely equal for all valves. To this end it is important that the tilt valve is accurately pivoted. With reference to FIGS. 3 and 4, and as indicated above, it can be seen that the locating legs 48 have a spherical profile at their contact face with the bore 48 of the seat. The centre of each sphere is at the centre of the sealing face 32 of the sealing member 22. As small a clearance as practical, without interfering, between the outside diameter of the spherical leg profile and the inside diameter of the bore 48 of the seat prevents the cap 36 from moving away from the centre of the seat 24 as it tilts. This arrangement provides another feature that helps to minimise inconsistencies that may arise between the movement of the diaphragm 54 and the angle of tilt of the sealing face 32.

The hard insert 42 also serves to improve the consistency of valve performance. Use of such a hard material to form a sealing surface 32 overcomes a problem encountered with a resilient material such as rubber. Rubber needs to be compressed in order to effect a good seal, requiring an additional closing force to be applied to the seal. This, in turn, gives a nonlinear component to the behaviour of the seal (particularly at its closure point) in relation to diaphragm movement. By way of contrast, a hard flat sealing surface will form a good seal on contact with another hard, flat surface, provided both sealing faces are sufficiently flat and smooth to prevent leaks between the contacting surfaces.

Not only must all valves open simultaneously and to the designed ratio, this behaviour should be consistent over the lifetime of the valves. Inclusion of the hard surface insert improves the wear-resistance of the sealing member 22. As the seal opens and closes, repeated contact with the sealing surface of the seat inevitably degrades the quality of the surface. The useful lifetime of the sealing member is therefore prolonged by inclusion of a hard insert. Thus, if the multiple valves within a demand valve open and close simultaneously and consistently when new, it is to be expected that this performance will be maintained for longer by inclusion of the hard insert 42.

Additional optional features of a demand valve for mixing gases in accordance with the present invention are included in FIGS. 1 to 5. The body of the valve 10 may include a wall 70 surrounding the diaphragm 54. This wall 70 deflects the flow of gas through the input connectors 16, 18 away from direct impact on the resilient portion 64 of the diaphragm, which could otherwise disrupt its smooth operation.

A cover 72 made of elastomeric material such as silicone rubber provides protection against knocks. A protrusion 74 of the cover extends through a hole 76 in the body of the valve to the vicinity of the stiff portion 62 of the diaphragm 54. Pressing on the cover at this protrusion 74 causes it to contact the diaphragm 54 and displace the central portion 62 to actuate the levers 40, 58. This therefore opens the tilt valves 12 manually. This feature is included to provide an operator with a means to test the presence of pressure on the valve: pressing the protrusion 74 creates a hiss as gas escapes. It also provides the option for a manual override to feed gas to a user. A space under the cover and around the protrusion 74 controls the amount of travel produced by pressing the back of the cover and therefore the flow generated. The local thickness of the cover, the material properties and the diameter of the space around the protrusion 74 control the stiffness of the operation. That is, how hard an operator has to press to achieve flow. These parameters can be adjusted in accordance with the application in order to provide the preferred balance between ease of testing and avoidance of accidental or unintended activation. Equivalently a return spring biased against a button or lever could perform the same function.

The pressure supplied to each seat 24 in a multiple valve assembly is a key factor in determining how much gas is delivered for a given tilting of each tilt valve 12. Regardless of the origin of the supply gas (cylinder, wall supply, etc), it is important that the pressure to the seats is accurately controlled. Unfortunately, the pressure available from many supply sources drops over the course of time. If multiple non-identical valves 12 are each connected to a different gas supply for mixing, then the different gas supplies will empty and hence lose pressure at a different rate. This will result in valve performances diverging and hence the composition of the gas mixture delivered into the main chamber 20 will also change with time. In order to avoid this, the ratio of absolute pressures to the seats 24 should be held constant over the design range of flows. This may be achieved in some cases by incorporation of a pressure regulator upstream of one or more of the tilt valves. The pressure regulator is designed to ensure that the ratio of gases from multiple tilt valves is maintained within the required limits over the whole range of flows that may be drawn from the demand valve. This may be achieved either by maintaining constant pressure, or by matching the input absolute pressure versus flow characteristics over the whole flow range.

It is of course not necessary for the pressure to each seat 24 to be the same. Indeed different pressures may be selected to control the flow of gas from the seats, and therefore the ratio of gases in the mixture delivered. For example, a lower pressure would cause less gas to be delivered from the respective tilt valve 12 for a given level of diaphragm 54 movement.

Figure 6:
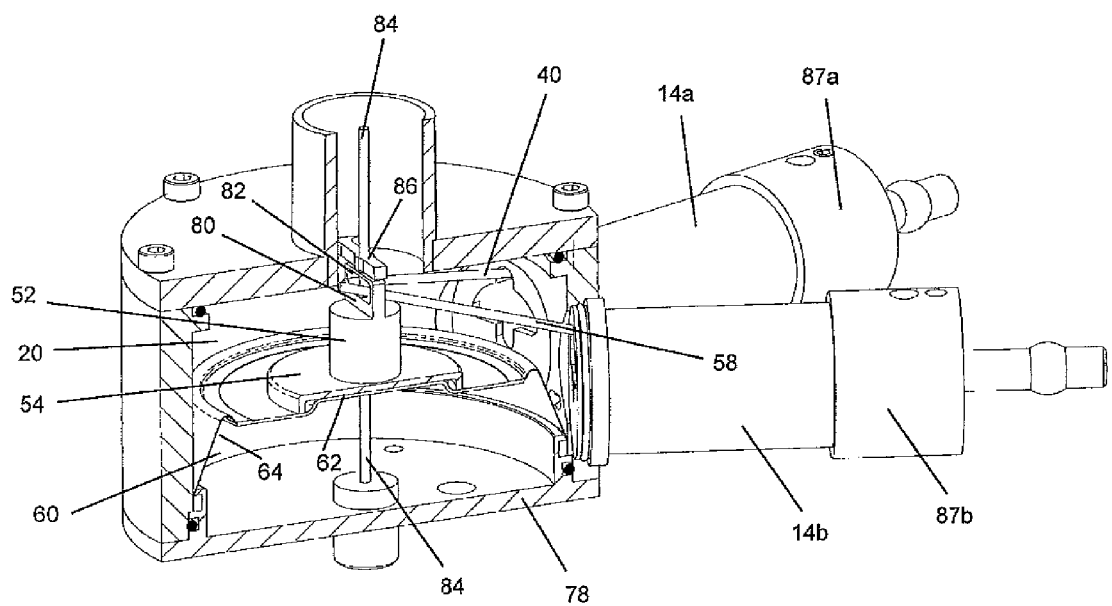
FIG. 6 is a cut-away view of the central region of a demand valve in accordance with this invention, showing guidance control of a diaphragm and levers.

In view of the need to maintain consistent performance between multiple tilt valves in a gas mixing demand valve over time and under a variety of operating conditions, FIG. 6 is an illustration of the diaphragm region of the demand valve showing its housing 78 cut away to reveal the structure of the assembly around the diaphragm 54 in an alternative embodiment of this invention. Again, components common to previous Figures are like referenced. In this embodiment, two gas input channels 14a, 14b enter the main chamber 20 adjacent each other, rather than from opposite sides. Accordingly, the levers 40, 58 converge at the diaphragm area at an acute angle, rather than at 180° as in the previous embodiments. Of course, this invention is not limited to any particular geometric orientation of the multiple tilt valves and input channels and any convenient arrangement may be selected. The contact pad 52 includes a rectangular extension 80 with an aperture 82 through which the actuation ends of the levers 40, 58 protrude. This aperture 82 serves to trap the levers 26, 58 and so prevent them coming out of register with the contact pad 52, for example, if the demand valve 10 is dropped. A shaft 84 is fixed to the diaphragm 54 and contact pad 52 and runs through holes 86 in the housing 78 both above and below the diaphragm 54. The shaft 84 serves to guide the diaphragm as its resilient portion 64 flexes to help it move in a parallel motion. This substantially eliminates the possibility that the diaphragm 54 tilts during flexing. Such tilting has the potential to move one lever 40, 58 further than another, therefore opening one valve to a greater extent. This would clearly result in one tilt valve 12 delivering more flow than intended, possibly to the extent that the gas composition falls outside the ratio required.

As an alternative embodiment (not shown), the levers 40, 58 are set to pass through respective apertures 82 at different heights within the contact pad, separated by a little over the diameter of the levers. The respective input channels 14a, 14b are also located at correspondingly different heights. The levers 40, 58 are then able to cross by one passing under the other, which permits the use of longer levers, without interference. This is advantageous as the longer lengths reduce the likelihood of the levers slipping or being knocked accidentally from the aperture if they are pushed back for any reason.

Also shown in FIG. 6 are first 87a and second 87b regulators in respective 14a, 14b input channels. It has been mentioned previously that regulators may be used to maintain supply pressure over time. A further advantage to their use is provided in situations in which it may be unacceptable to deliver one gas in the absence of the other. For example when mixing anaesthetic gas and oxygen, anaesthetic gas alone may kill a patient. If the gas that may be delivered alone (oxygen in this example) is controlled by the first regulator 87a and the gas that is unacceptable alone (anaesthetic in this example) is controlled by the second regulator 87b, then the first 87a and second 87b regulators should be arranged as follows. The first regulator 87a is spring biased to deliver the desired flow whereas the second regulator 87b is piloted by the output of the first such that its output matches or is proportional to the pressure of the first regulator. In this way, if the supply of oxygen falls or fails, the output of the first regulator falls or stops. The second regulator output therefore also falls or stops. The regulator output pressure of the anaesthetic is accordingly matched to that of the oxygen, maintaining the ratio of the two in the case of falling oxygen supply and preventing dispensing of further anaesthetic if the oxygen supply fails.

Figure 7:
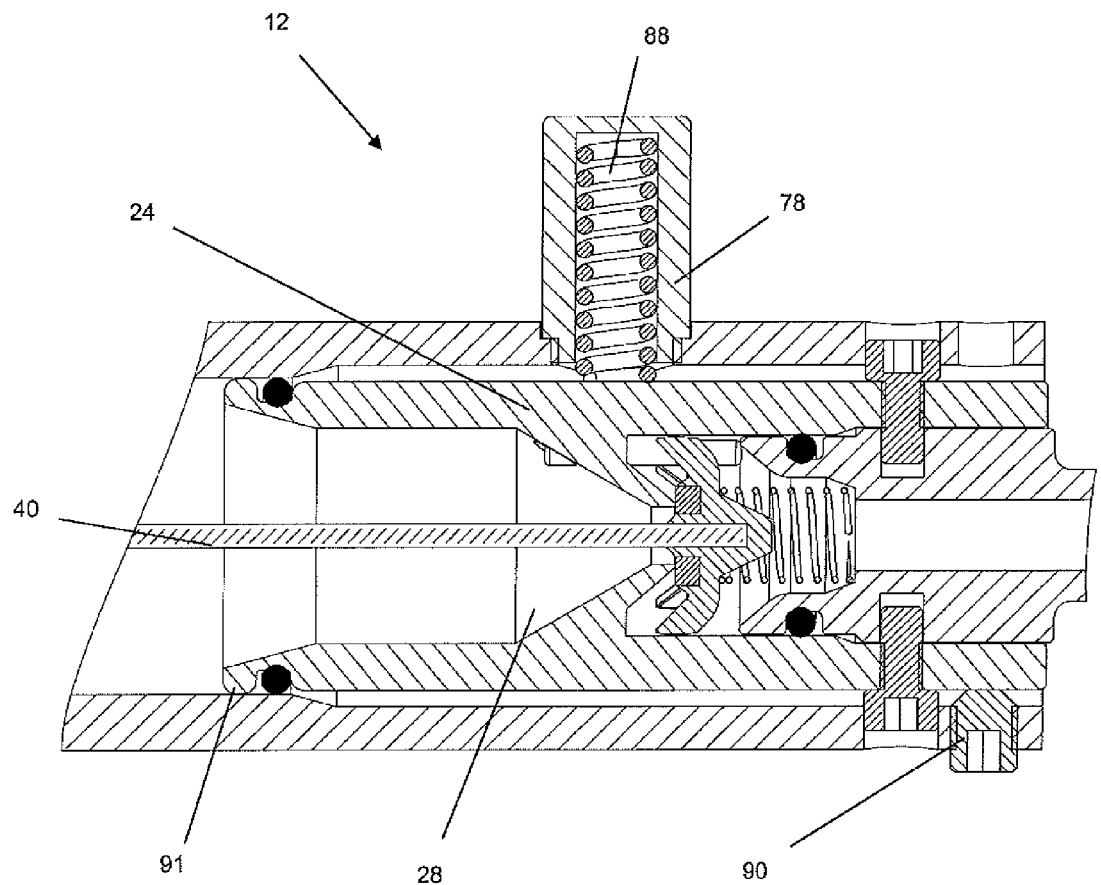
FIG. 7 is a schematic illustration of an end part of a tilt valve for use with this invention, showing adjustment mechanism(s) for allowing pre-setting of control valve characteristics in order to improve consistency of behaviour for multiple valves.

FIG. 7 is a schematic illustration of an area of a demand valve around the seat 24 of a tilt valve 12, showing an adjustment mechanism for allowing pre-setting of tilt lever position when the tilt valve is closed. This, in turn, sets the diaphragm position at which the tilt valve will open and gas starts to flow. The adjustment mechanism includes a spring 88 retained in the housing 78 to one side of the seat 24 and an adjuster screw 90 extending through the housing 78 to the other side of the seat 24. The spring 88 pushes the seat 24 towards the screw 90 and a pivot contact point 91, ensuring contact is maintained. Turning the adjuster screw 90 moves the right (in the diagram) side of the seat up and down about the pivot point 91, while the far left side is unmoved. This varies the angle of the passage 28 through the seat and hence also of the lever 40. In this way the position of the actuation end of the lever is adjusted in relation to its contact point with the diaphragm. All tilt valves within a mixing demand valve can be adjusted incrementally until it is ensured that the lever position of each is such that all valves start to open at the same time. This helps to balance out inconsistencies arising through manufacturing tolerances.

Alternatively, it may be arranged such that one valve opens slightly before any others. This is useful in applications such as those in which an anaesthetic gas is being delivered with oxygen. It is acceptable for oxygen to be delivered on its own, but not the anaesthetic, and accordingly the safest arrangement is to ensure that the oxygen starts to be delivered first.

Figure 11:
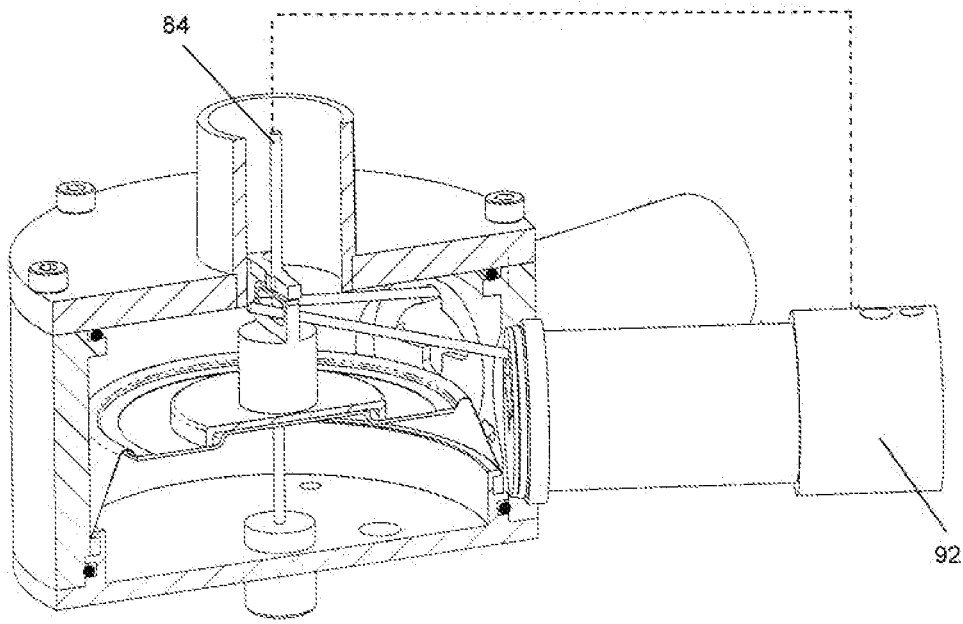
FIG. 11 is a cut-away view of the central region of an alternative embodiment of a demand valve in accordance with this invention.

A further embodiment, also beneficial to situations in which oxygen is to be delivered with an anaesthetic gas, is shown in FIG. 11. This embodiment includes a pressure detector 92 located in the oxygen gas connection channel. This may be provided by a piston moved against a spring in response to the presence of as pressure. If the flow in the oxygen channel drops, then the pressure acting on the piston falls and the bias of the spring moves the piston to return the diaphragm (for example by movement of the connected shaft 84 shown in FIG. 6 and FIG. 11) to its relaxed position. Alternatively, the spring may be arranged to act directly on the diaphragm and return it to its relaxed position in the absence of oxygen pressure. Accordingly, both tilt valves will be closed. This provides a fail safe mechanism by which flow is completely cut if one gas supply runs out, and an operator can be alerted.

Figure 5:
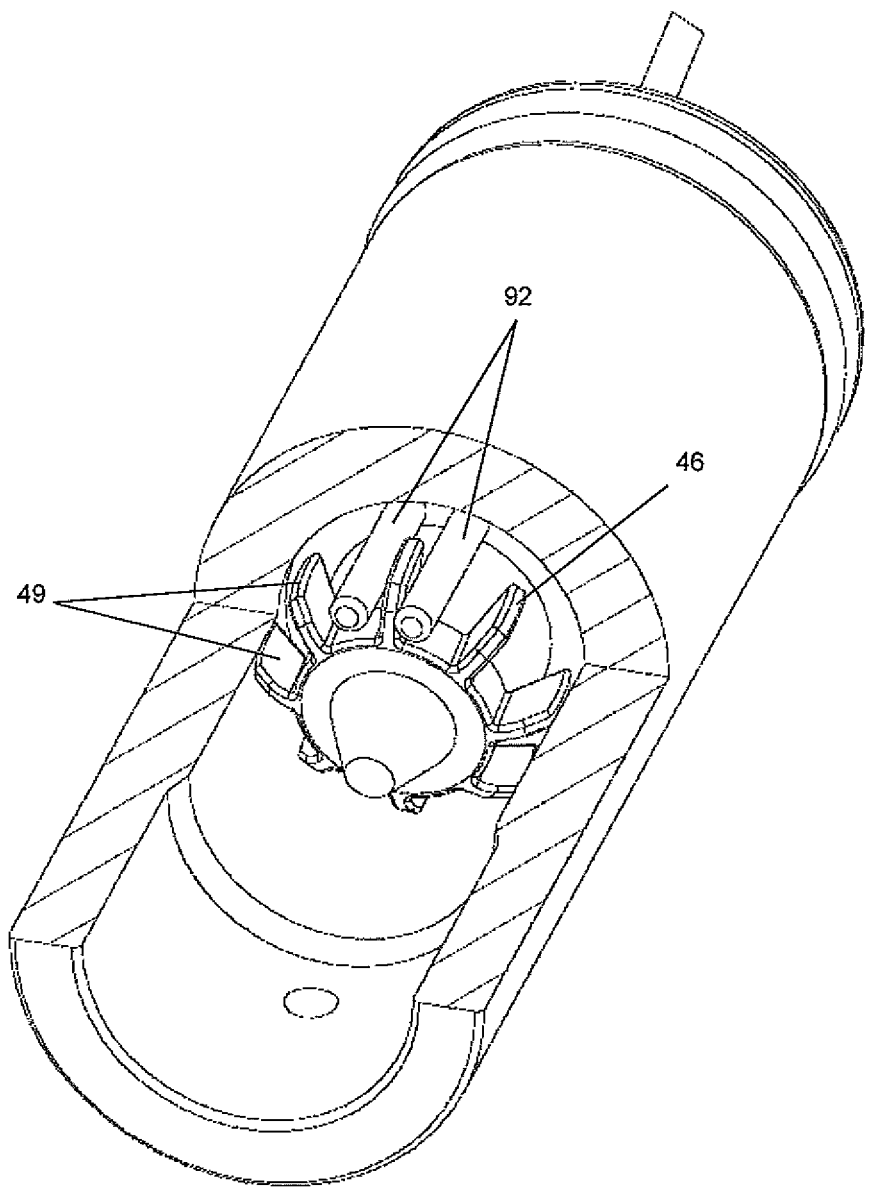
FIG. 5 is a cut-away, perspective view of a sealing part of the tilt valve mechanism located in a bore, suitable for use with the demand valve of this invention.

FIG. 5 is a perspective view of the tilt valve region with casing shown cut away to reveal the structure of the tilt valve cap 36. The spherical profile of the locating legs 48 has been described previously, with the result that the cap 36 is as free from friction as possible to tilt away from the seat 24. Friction is undesirable as not only does it increase the force necessary to be applied to open (i.e. inhalation pressure) and close the seat, it also introduces a possible inconsistency between different valve assemblies. In some cases, it can cause a valve to stick open. As indicated previously, it is important that multiple tilt valves within each demand valve function as uniformly as possible over the operating ranges required. The free-moving cap however may also rotate. This is undesirable in any case, but particularly if the tilt valves have been adjusted by the adjustment mechanism shown in FIG. 7 to account for a bending of the lever. In this situation the adjustments would no longer ensure simultaneous opening of multiple tilt valves. One or more pins 90 are therefore attached to the housing 78 to engage with one of the locating legs 48 and so prevent any rotational movement. The contact points of the pins 90 are parallel with the direction of tilt in order to minimise friction.

Figure 8A:
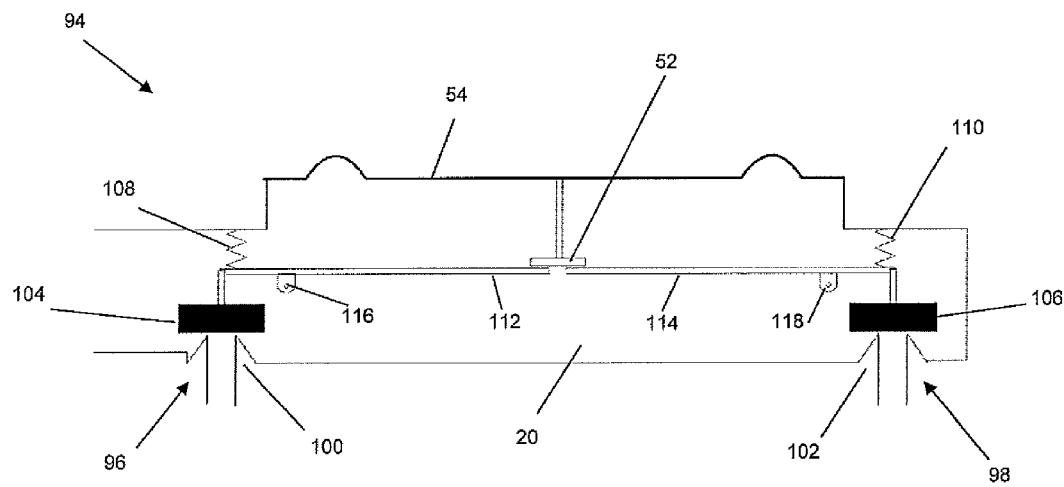
FIGS. 8a and 8b illustrate schematically two further embodiments of this invention, which employ different valve types to control the gas flow.
Figure 8B:
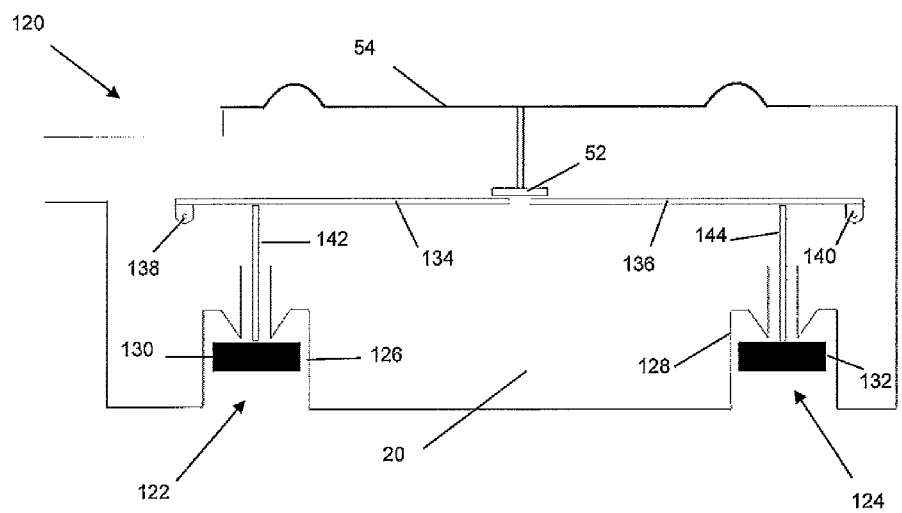

FIGS. 8a and 8b show schematically two further embodiments of this invention, which employ different lever-operated valves to control the gas flow. As with previous embodiments, components common to previous Figures are like referenced.

With reference first to FIG. 8a, the demand valve 94, comprises first 96 and second 98 lever-operated valves to control gas flow from separate pressure supplies (not shown) to the main chamber 20. Each lever-operated valve 96, 98 essentially consists of a seat 100, 102, which is sealed by means of a sealing member 104, 106. In this embodiment, unlike previous embodiments, the valves 96, 98 are sealing against the pressure of the supply. Accordingly a spring 108, 110 is arranged to bias each sealing member 104, 106 towards its respective seat 100, 102 with a force that is just sufficient to overcome supply gas pressure on the seals. For each valve 96, 98, an L-shaped lever 112, 114 is attached to the sealing member 104, 106 at the end of its short arm, its long arm extending from the other end of the short arm to the central portion of the actuating diaphragm 54. The lever 112, 114 pivots about a point towards the sealing member end of the long arm. Thus, when the diaphragm 54 is flexed forwards as a result of a drop in pressure in the main chamber 20, the levers 112, 114 pivot to lift the sealing members 104, 106 away from their respective seats 100, 102 and so to open the valves 96, 98. As with previous embodiments, the mechanics of the lever is exploited to ensure that a small force/large displacement of the diaphragm 54 causes a large force/small displacement at the seals.

With reference now to FIG. 8b, the demand valve 120 of this embodiment of the invention, comprises first 122 and second 124 lever-operated valves to control gas flow from separate pressure supplies (not shown) to the main chamber 20. Each lever-operated valve 122, 124 consists of a seat 126, 128, which is sealed by means of a sealing member 130, 132. In this embodiment supply pressure serves to bias the valves 122, 124 in a closed configuration. For each valve 122, 124, a lever 134, 136 extends from the central portion of the actuating diaphragm 54 to a pivot point 138, 140. A pusher 142, 144 is attached to each levers 134, 136 close to its pivot point 138, 140 and to the sealing member 130, 132 of the respective valve 122, 124. In this embodiment, when the pressure drops in the main chamber 20 as a result of inhalation, the diaphragm 54 is flexed to displace one end of the levers 134, 136. This causes the levers 134, 136 to rotate about their pivot points 138, 140 and so to move the pushers 142, 144 towards the valves 122, 124, tilting the sealing members 130, 132 away from their respective seats 122, 124.

Figure 9:
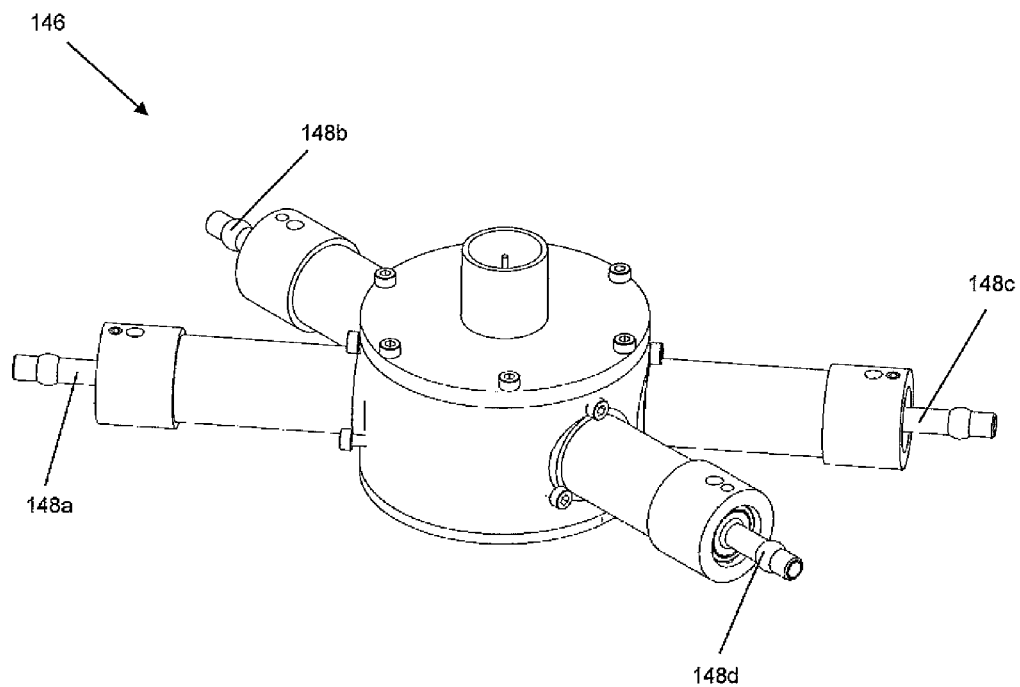
FIG. 9 is a perspective view of a demand valve in accordance with the present invention, showing four inlet channels.

FIG. 9 is a perspective view of a further embodiment 146 of a demand valve for mixing gas in accordance with the present invention. In this embodiment, four 148a, b, c, d gas connection channels are illustrated. Each has a respective valve (not shown), which controls gas flow from a supply into the main chamber. Accordingly, this embodiment is suitable for mixing gas from up to four different sources (not all channels need be used) in proportions determined by the parameters of each valve and gas supply. It will be clear that any number of input channels may be included in a demand valve constructed in accordance with this invention, although there is likely to be a practical limit set by the space available. Furthermore the channels may be arranged in any convenient geometry about the main chamber. The two and four channels versions described herein are by way of example only.

The invention claimed is:

1. A demand valve for gas mixing, the valve comprising at least two gas connection channels, each containing a respective flow control valve, for supplying gas to a main chamber wherein:
   the demand valve includes an actuation means that is responsive to a pressure change in the main chamber;
   each flow control valve is a lever valve that is operated by a respective lever, each lever extending independently of the at least one other lever from a central region of the actuation means to a seal of the respective flow control valve; and
   the actuation means is a common actuation means whereby in a single movement it is operable to move the respective levers such that they each displace the seal from a seat of its respective flow control valve so as to open and close proportionally in a substantially constant ratio the at least two flow control valves.

2. A demand valve according to claim 1 wherein the seat of one control valve is of a different size to that of at least one other valve.

3. A demand valve according to claim 1 wherein the lever operating one flow control valve is a different length than at least one other operating lever.

4. A demand valve according to claim 1 wherein the valve includes a pressure detector located in one of the gas connection channels and acting on the common actuation means and arranged such that if the pressure in the gas connection channel drops below a predetermined level, the actuation means is moved to close the at least two flow control valves.

5. A demand valve according to claim 1 wherein the valve includes first and second regulators located in respective gas connection channels, the first regulator being piloted by the second and arranged such that if the output of the second regulator falls below a predetermined level, the output of the first regulator falls to zero.

6. A demand valve according to claim 1 wherein the valve comprises multiple gas connection channels with inlets distributed around walls of the main chamber.

7. A demand valve according to claim 1 wherein the common actuation means is a diaphragm.

8. A demand valve according to claim 7 wherein the valve includes guidance means connected to the diaphragm whereby tilting of the diaphragm is hindered.

9. A demand valve according to claim 7 wherein the diaphragm is attached to a contact pad, the contact pad being positioned to contact the levers to operate the flow control valves.

10. A demand valve according to claim 9 wherein the contact pad includes one or more apertures through which the levers extend.

11. A demand valve according to claim 1 wherein each lever extends to a cap comprising a sealing face for sealing against the seat of the respective valve and a protrusion is located in a bore of each gas connection channel so as to interengage with the cap and inhibit rotational movement of the cap and connected lever.

12. A demand valve according to claim 11 wherein the sealing face of the cap includes an insert made of a harder material than that of the remainder of the cap.

13. A demand valve according to claim 11 wherein each flow control valve includes a respective adjustment mechanism that is operable to displace the flow control valve and so to adjust its respective lever such that each lever may be repositioned with respect to the actuation means, independently of the at least one other lever.

14. A demand valve according to claim 11 wherein each control valve is a tilt valve.

15. A demand valve according to claim 14 wherein the cap includes locating means for holding the cap centrally in a bore of the gas connection channel wherein lateral movement of one end of the lever by the actuation means effects a pivotal tilt of the cap within the bore such that the sealing face lifts partly off the seat.

16. A demand valve according to claim 15 wherein the lever extends through the seat of the respective valve.

17. A demand valve according to claim 16 wherein the tilt valve also includes biasing means set to bias the cap against the seat.

18. A demand valve according to claim 15 wherein the protrusion interengages with the locating means of the cap.

19. A demand valve according to claim 18 wherein the protrusion is a pin or pins.

20. A demand valve according to claim 18 wherein the locating means comprises a series of slots or protrusions.

21. A method of mixing gases on demand, the method comprising the steps of:
(a) changing pressure in a main chamber of a demand valve in response to a user's respiration; and
(b) moving a common actuation means in response to the pressure variation at step (a), the common actuation means being operable to displace at least two levers, each lever extending, independently from the at least one other lever, from the actuation means to respective flow control valves such that the flow control valves open and close proportionally in a substantially constant ratio, the at least two flow control valves being pre-positioned in respective gas connection channels taking gas from respective independent sources.

22. A demand valve for gas mixing, the valve comprising at least two gas connection channels, each containing a respective flow control valve, for supplying gas to a main chamber wherein:
the demand valve includes an actuation means that is responsive to a pressure change in the main chamber;
each flow control valve is a lever valve that is operated by a respective lever, each lever extending independently of the at least one other lever from a central region of the actuation means to a cap comprising a sealing face for sealing against the seat of the respective flow control valve;
a protrusion is located in a bore of each gas connection channel so as to interengage with the cap and inhibit rotational movement of the cap and connected lever; and
the actuation means is a common actuation means whereby in a single movement it is operable to move the respective levers such that they each displace the seal from a seat of its respective flow control valve so as to open and close proportionally in a substantially constant ratio the at least two flow control valves.

* * * * *

UNITED STATES PATENT AND TRADEMARK OFFICE
CERTIFICATE OF CORRECTION

PATENT NO. : 8,443,826 B2 Page 1 of 1
APPLICATION NO. : 12/601421
DATED : May 21, 2013
INVENTOR(S) : Andrew Tatarek It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 771 days.

Signed and Sealed this

Eighth Day of September, 2015

Michelle K. Lee
*Director of the United States Patent and Trademark Office*